(12) United States Patent
Paci et al.

(10) Patent No.: US 9,073,957 B2
(45) Date of Patent: Jul. 7, 2015

(54) DERIVATIVES OF OXAZAPHOSPHORINES THAT ARE PRE-ACTIVATED, USE AND METHOD OF PREPARATION

(75) Inventors: Angelo Paci, Meudon (FR); Thierry Martens, La Queue en Brie (FR); Michael Rivard, Creteil (FR); Patrick Couvreur, Villebon sur Yvette (FR); Didier Desmael, Fresnes (FR); Joachim Caron, Les Ulis (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 0 days.

(21) Appl. No.: 13/992,404

(22) PCT Filed: Dec. 9, 2011

(86) PCT No.: PCT/FR2011/052914
§ 371 (c)(1),
(2), (4) Date: Jun. 7, 2013

(87) PCT Pub. No.: WO2012/076824
PCT Pub. Date: Jun. 14, 2012

(65) Prior Publication Data
US 2013/0261088 A1    Oct. 3, 2013

(30) Foreign Application Priority Data
Dec. 10, 2010  (FR) .................................. 10 60350

(51) Int. Cl.
*C07F 9/02* (2006.01)
*A01N 57/36* (2006.01)
*A61K 31/66* (2006.01)
*C07F 9/6584* (2006.01)

(52) U.S. Cl.
CPC .................................. *C07F 9/65846* (2013.01)

(58) Field of Classification Search
None
See application file for complete search history.

(56) References Cited

FOREIGN PATENT DOCUMENTS

GB    2095256 A    9/1982
JP    55154984 A  * 12/1980

OTHER PUBLICATIONS

Harada et al. English Abstract.*
Hirando, T. et al. "Synthesis of activated cyclophosphamide derivatives bearing functional groups" *Tetrahedron Letters*, 1979, pp. 883-886, No. 10, XP002632109.
Zon, G. et al. "NMR Spectroscopic Studies of Intermediary Metabolites of Cyclophosphamide. A comprehensive Kinetic Analysis of the Interconversion of *cis*- and *trans*-4-Hydroxycyclophosphamide with Aldophosphamide and the Concomitant Partitioning of Aldophosphamide between Irreversible Fragmentation and Reversible Conjugation Pathways" *Journal of Medicinal Chemistry*, 1984, pp. 466-485, vol. 27, No. 4.
Qiu, R. et al. "ABCC2-Mediated Biliary Transport of 4-Glutathionylcyclophosphamide and Its Contribution to Elimination of 4-Hydroxycyclophosphamide in Rat" *The Journal of Pharmacology and Experimental Therapeutics*, 2004, pp. 1204-1212, vol. 308, No. 3.
Reddy, L. H. et al. "Novel Approaches to Deliver Gemcitabine to Cancers" *Current Pharmaceutical Design*, 2008, pp. 1124-1137, vol. 14.
Written Opinion in International Application No. PCT/FR2011/052914, Mar. 26, 2012, pp. 1-8.

* cited by examiner

*Primary Examiner* — Dennis Heyer
*Assistant Examiner* — Daniel M Podgorski
(74) *Attorney, Agent, or Firm* — Saliwanchik, Lloyd & Eisenschenk

(57) ABSTRACT

The present invention relates to novel derivatives of oxazaphosphorines that are pre-activated, to the methods for preparing same, to the pharmaceutical compositions containing same and to the therapeutic use thereof, in particular for treating cancer.

23 Claims, No Drawings

DERIVATIVES OF OXAZAPHOSPHORINES THAT ARE PRE-ACTIVATED, USE AND METHOD OF PREPARATION

CROSS-REFERENCE TO RELATED APPLICATION

This application is the U.S. national stage application of International Patent Application No. PCT/FR2011/052914, filed Dec. 9, 2011.

The present invention relates to the field of medicine, in particular that of oncology. It relates to novel derivatives of pre-activated oxazaphosphorine drugs.

Drugs from the oxazaphosphorine class are alkylating and immunosuppressive antineoplastic agents (CPM) used in the treatment of cancer (for example, lymphomas and leukemias, sarcomas, solid tumors, notably of the lung, breast, prostate and ovaries). Ifosfamide (IFM) and cyclophosphamide (CPM) are prodrugs whose cytotoxic activity is associated with cytochrome P450-dependent metabolic activation introducing a hydroxyl group at position 4. The toxicity of oxazaphosphorines (ifosfamide and cyclophosphamide) is urological and results from an accumulation of acrolein, a metabolite formed after release of the alkylating mustard. In addition, these agents also cause neurotoxicity and nephrotoxicity due to the presence of chloroacetaldehyde, a metabolite produced by oxidation of the side chains of the molecule via the action of cytochrome P450. Acrolein-related toxicity can be attenuated by coadministration of sodium mercaptoethanesulfonate.

A route of synthesis by electrochemistry of methoxylated derivatives at position 4 has been described (Paci et al., 2001, *Bioorg Med Chem Lett*, 11, 1347-1349). These derivatives are considered to be pre-activated analogues since they exhibit cytotoxic activity that is comparable to that of the oxidized metabolite and much higher than the initial, non-oxidized products. In fact, they allow the release of alkylating mustards without intervention of cytochromes P450.

Furthermore, other oxazaphosphorine derivatives have been developed with the aim of reducing their toxicity. In particular, the toxigenic oxidation of the methylated side chains of these derivatives is eliminated or limited all while retaining their alkylating power. A review can be found in Giraud et al. (2010, Expert Opin Drug Metab Toxicol, 6, 919-938). By way of illustration, two cyclophosphamide derivatives, namely, glufosfamide and mafosfamide, as well as C7,C9-dimethyl-ifosfamide may be mentioned.

Patent application GB2095256 describes oxazaphosphorin-4-thio-alkanesulphonic acids, in particular derivatives of cyclophosphamide. Hirano et al. (Tetrahedron Letters, 10, 883-886) also describe cyclophosphamide derivatives substituted at position 4 obtained by reacting 4-hydroperoxycyclophosphamide with a mercaptoalkane.

GB2095256 and Hirano et al. do not describe any ifosfamide derivative substituted at position 4.

Oxazaphosphorine derivatives, and in particular derivatives of ifosfamide, having more potent cytotoxic activity or a more targeted action would be very useful, thereby reducing the required dose and consequently reducing the toxic side effects.

The inventors have developed a method for preparing oxazaphosphorine derivatives that are pre-activated and have a vectorization or formulation group at position 4.

A vectorization group can allow the drug to be targeted to the target tissue (tumor tissue or cancer cells) thereby making it possible to reduce the doses to be administered all while retaining good therapeutic efficacy.

A formulation group can help protect the active moiety from degradation before it reaches the target tissue and/or modulate its activity by modulating the rate of release of the alkylating mustard, in particular by stabilizing the molecule. Indeed, the oxazaphosphorines are drugs that degrade rapidly. In summary, this group can modify the physicochemical, pharmacokinetic or pharmacodynamic properties of oxazaphosphorines.

The invention therefore relates to a method for preparing a derivative of pre-activated oxazaphosphorines of formula (I),

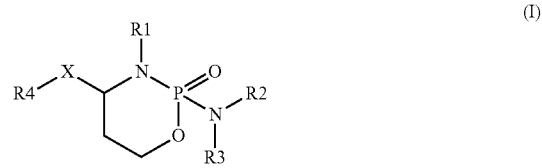

wherein

X is O or S;

R1 and R2 are independently H, —CH(CH$_3$)—CH$_2$—Cl or —(CH$_2$)$_2$—Cl, provided that at least one of the two is —CH(CH$_3$)—CH$_2$—Cl or —(CH$_2$)$_2$—Cl;

R3 is —CH(CH$_3$)—CH$_2$—Cl or —(CH$_2$)$_2$—Cl; and,

R4 is a formulation or vectorization group comprising at least three carbon atoms; comprising providing a compound of formula (II)

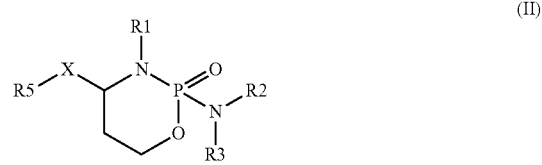

wherein R1, R2 and R3 are defined as in formula (I), and R5 is a methyl or ethyl; and, reacting the compound of formula (II) with an alcohol or thiol of formula (III) R4-XH, wherein X and R4 are defined as in formula (I), in the presence of a Lewis acid.

In the context of the present invention, "formulation group" is understood to mean a group allowing to stabilize the oxazaphosphorine and in particular to decrease the rate of release of the alkylating mustard. In particular, the half-life of the pre-activated oxazaphosphorine can be increased by increasing the number of carbons in the formulation group. In addition, this group can enable or improve the stability of the oxazaphosphorine for parenteral administration particularly intravenous. In a most preferred embodiment, said group allows the formation of nanoparticles, micelles or liposomes.

In the context of the present invention, "vectorization group" is understood to mean a group allowing targeting to the tumor, that is to say, more specifically delivering the oxazaphosphorine to the tumors or cancerous cells in order to enhance the specificity of action and diminish the side effects.

Optionally, the group contains at least 4, 5, 6, 7 or 8 carbons.

The chemical reaction can be described in more detail in the following diagram.

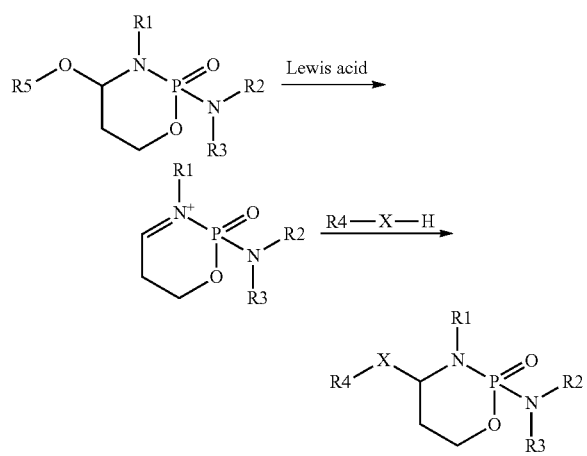

Thus, it can be broken down into a step of forming the iminium and a step of reacting with the nucleophile R4-XH (also called amidoalkylation). In particular, the Lewis acid can be TMSOTf, $AlCl_3$ or $BF_3.OEt_2$. In a preferred embodiment, the Lewis acid is preferably $BF_3.OEt_2$. Preferably, the $BF_3$ Lewis acid is used with $O(CH_2—CH_3)_2$. The ratio between the number of moles of Lewis acid and the number of moles of compound (II) is generally less than 1.5. A molar ratio less than 1.5 includes a molar ratio less than 1.5; 1.4; 1.3; 1.2; 1.1; 1.0; 0.9; 0.8; 0.7; 0.6 and 0.5. In particular, the ratio between the number of moles of Lewis acid and the number of moles of compound (II) can be comprised in a range from 0.01 to 0.7, preferably from 0.05 to 0.5. As an example, the reaction can be carried out in the presence of 0.05 Eq to 0.5 Eq of $BF_3.OEt_2$ when R4-XH is pentan-1-ol or in the presence of approximately 1.1 Eq when R4-XH is squalenol.

Although R5 may be a methyl or ethyl group, methyl is preferred.

The solvent must be appropriate to dissolve the compounds of formula (II) and (III). For example, depending on the reagents involved, the solvent can be THF (tetrahydrofuran) or $CH_2Cl_2$ (dichloromethane). It goes without saying that one will avoid the use of a nucleophilic solvent such as an alcohol which may compete with the compound of formula (III) (that is to say, R4-XH). In a preferred embodiment, the solvent is dichloromethane ($CH_2Cl_2$).

The reaction can be carried out in a temperature range comprised between −80° C. and 0° C., preferably starting at about −78° C. The reaction time can be adjusted according to the compounds and may for example be between 30 minutes and 12 hours, preferably about 60 minutes.

Preferably, the XH function is an alcohol or a primary thiol.

The compounds of formula (II) can be prepared by anodic oxidation, in particular such as described in the article by Paci et al. (2001, *Bioorg Med Chem Lett*, 11, 1347-1349). In particular, they can be prepared by anodic oxidation in methanol or ethanol with a carbon graphite electrode in the presence of tetraethylammonium tosylate ($Et_4NOTs$) or tetraethylammonium tetrafluoroborate ($TEABF_4$).

As illustrated in the examples, the method according to the invention is particularly suitable for preparing oxazaphosphorine compounds of formula (II) wherein R2 is H and R1 and R3 are selected independently from each other from —CH(CH₃)—CH₂—Cl and —(CH₂)₂—Cl.

Any type of R4-XH compound can be used to carry out the method according to the invention. Preferences concerning the R4 group are presented in more detail below.

Note that the yields of the method according to the invention are generally higher than those obtained by the conventional synthesis method of electrochemically oxidizing the oxazaphosphorine compound in the presence of the R4-XH nucleophile.

In a surprising manner, the Applicant showed that the chain length of the R4 group is not a limiting criterion for the reaction since it is possible to conjugate alkyl derivatives of very different chain lengths such as pentanol or tris-nor squalenol with similar yields and reaction times.

In a particular embodiment, the steps of providing a compound of formula (II) and the reaction in the presence of a Lewis acid with a R4-XH compound can be carried out jointly in the same reaction medium.

Alternatively, compounds of formula (I) can be prepared by a direct method of anodic oxidation provided that the size of the R4 moiety is limited to 7 carbons. This is not the preferred method because it requires a large amount of nucleophile and requires the use of compounds resistant to oxidizing conditions. In this embodiment, methanol or ethanol will be replaced by the compound of formula R4-OH.

The present invention also relates to novel compounds of formula (I)

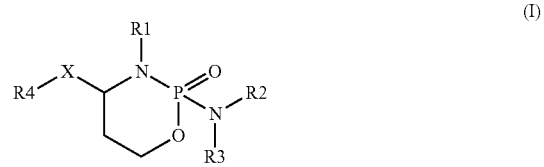

(I)

wherein

X is O or S;

R1 and R2 are independently H, —CH(CH₃)—CH₂—Cl or —(CH₂)₂—Cl, provided that at least one of the two is —CH(CH₃)—CH₂—Cl or —(CH₂)₂—Cl;

R3 is —CH(CH₃)—CH₂—Cl or —(CH₂)₂—Cl; and,

R4 is a formulation or vectorization group of at least 3 carbons.

In one embodiment, R1 is H and R2 and R3 are independently —(CH₂)₂—Cl or —CH(CH₃)—CH₂—Cl. In this case, compound (I) or (II) is a derivative of cyclophosphamide. Preferably, R2 and R3 are —(CH₂)₂—Cl.

In another embodiment, R1, R2 and R3 are independently —(CH₂)₂—Cl or —CH(CH₃)—CH₂—Cl. In this case, compound (I) or (II) is a derivative of trofosfamide. Preferably, R1, R2 and R3 are independently —(CH₂)₂—Cl.

The invention more particularly relates to derivatives of ifosfamide. Thus, in a preferred embodiment, R2 is H and R1 and R3 are independently —(CH₂)₂Cl or —CH(CH₃)CH₂Cl. In some embodiments, R1 and R3 are —(CH₂)₂Cl.

In other embodiments, R1 and R3 are —CH(CH₃)CH₂Cl.

In a further embodiment, R1 is —(CH₂)₂Cl and R3 is —CH(CH₃)CH₂Cl. In another embodiment, R3 is —(CH₂)₂Cl and R1 is —CH(CH₃)CH₂Cl.

Generally, R4 can comprise a linker or spacer, said linker or spacer being located at the proximal end and therefore attached to the X group. Linkers and spacers are well known to one of skill in the art, such as cysteine derivatives. Optionally, they allow introduction of the XH group. Preferably, the XH group is a primary thiol or alcohol.

The formulation or vectorization groups are well known in the field. The following articles may be mentioned by way of illustration: Singh et al. (2008, *Curr Med Chem*, 15, 1802-1826), Das et al. (2009, *Curr Opin Drug Deliv*, 6, 285-304), etc.

Preferably, R4 in formulas (I) and (III) is selected from the following groups or comprises such groups:

- a hydrocarbon group of 3 to 40 carbon atoms, preferably from 3 to 30 carbon atoms (preferably 4, 5, 6, 7 or 8 to 30 carbon atoms), saturated or unsaturated, linear or branched, optionally substituted by one or more groups selected from the group consisting of —OR, —C(O)OR, —OC(O)R, —OC(O)OR, —C(O)R, —NRR', —C(O)NRR', —NC(O)R, —NRC(O)R', —SR, halogen, cyano (—CN), aryl, heteroaryl, arylalkyl; R and R' being hydrogen or a $C_1$-$C_3$ alkyl;
- a lipid;
- an amino acid;
- a peptide or a protein, preferably a peptide;
- a vitamin;
- an aptamer;
- a polymer; and,
- a polyol.

"$C_1$-$C_3$ alkyl" is understood to mean methyl, ethyl, propyl or isopropyl.

"Halogen" is understood to mean a halogen atom selected from the group consisting of Cl, Br, I and F.

"Aryl" is understood to mean an aromatic hydrocarbon group, substituted or not, preferably having 6 to 14 carbon atoms. Preferably, the aryl groups according to the present invention are selected from the group consisting of phenyl, naphthyl (for example 1-naphthyl or 2-naphthyl), biphenyl (for example, 2-, 3- or 4-biphenyl), anthryl or fluorenyl. Phenyl groups, substituted or not, are particularly preferred.

"Heteroaryl" is understood to mean an aromatic hydrocarbon group having one or more heteroatoms such as nitrogen, sulfur and oxygen, substituted or unsubstituted, preferably having 6 to 14 carbon atoms. Examples that may be cited are pyridinyl, pyridazinyl, pyrimidyl, pyrazyl triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, oxazolyl or isoxazolyl groups, etc.

"Arylalkyl" is understood to mean an aryl group substituted by an alkyl group. The terms "alkyl" and "aryl" are as defined previously. Examples of arylalkyl groups include tolyl, mesithyl and xylyl.

When R4 is a hydrocarbon group of 3 to 30 carbon atoms, R4 is for example a $C_3$-$C_7$ alkyl or alkene, linear or branched, optionally comprising one or more hydroxyl groups or a $C_3$-$C_7$ hydroxy acid residue. Preferably, R4 is linear. In a particular embodiment, R4 can be selected from the group consisting of pentyl, hexyl or heptyl, which may optionally include one or more unsaturations and be substituted by one or more hydroxyl groups. Preferably, R4 can be selected from a pentyl, hexyl or heptyl, which may optionally comprise an unsaturation and be substituted by a hydroxyl group. Preferably, the hydroxyl groups are not primary, but rather secondary or tertiary.

Specific compounds of the invention are the following:

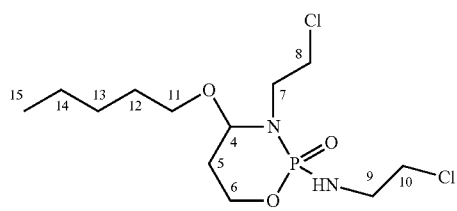

36

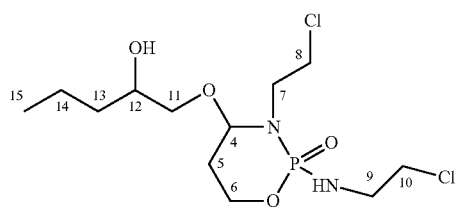

38

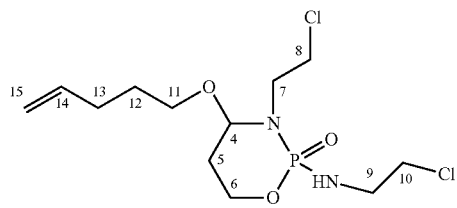

40

When R4 is a lipid, it can be selected from the group consisting of fatty acids, eicosanoids, acylglycerols, phosphoacylglycerols, sphingolipids, sterols, and saccharolipids. In particular, R4 can be a fatty acid, saturated or unsaturated, linear or branched. Preferably the fatty acid has a chain of at least 18 carbons. More particularly, the fatty acid has an unsaturated and branched chain of at least 18 carbons. In a preferred embodiment, R4 is squalenoyl. In fact, squalene is of great interest in drug formulation (WO2006/090029). Alternatively, R4 can be a sterol. In a preferred embodiment, R4 is cholesterol. The present invention more particularly considers the lipid groups allowing the formation of nanoparticles, micelles or liposomes, especially in a polar solvent, preferably an aqueous phase. Such lipids are well known to one of skill in the art. These include, but are not limited to, cholesterol, phospholipids and squalenoyls.

When R4 is an amino acid, the amino acid can be natural or not.

When R4 is a peptide, any peptide known to allow targeting of tissues or cells, in particular tumors and cancer cells or neovascularization, often via cellular receptors, is suitable for the present invention. These peptides are well known to one of skill in the art and comprise peptidomimetics. By way of illustration, one may cite those targeting peptides or peptidomimetics allowing tumor targeting (WO2008/120098, WO2000/032237) such as those comprising an asparagine-glycine-arginine (NGR), glycine-serine-leucine (GSL) or arginine-glycine-aspartate (RGD) moiety (WO2008/045252, WO2006/095234, WO2005/123767, WO2002/026776, WO98/010795) or those described in application WO00/032237. In addition, peptides have been described to target a particular organ, for example the lung (WO2003/105907), to cross the blood-brain barrier (WO2003/070755, WO2003/059394, WO2003/026701, WO2003/026700, WO2002/067994, WO00/032236), to facilitate cell or nuclear penetration of the drug (WO2005/016960, WO2001/064738). R4 can also be a lectin, EGF (epidermal growth factor), or an antibody or a fragment thereof having the antigen binding domain, preferably an antigen specific of the cancer or of the targeted tissue or organ.

When R4 is a polyol, a saccharide or polysaccharide will be preferred. For example, R4 can be glucose. Alternatively, R4 can be a chitosan.

When R4 is a vitamin, folic acid will be preferred. Folic acid is commonly used to vectorize drugs, particularly in the field of oncology. Alternatively, R4 can be vitamin B12.

When R4 is an aptamer, said aptamer will preferably be specific for a tumor antigen.

When R4 is a polymer, a polymer allowing the formation of nanoparticles will be preferred. Such polymers are well known to one of skill in the art. It may be mentioned by way of illustration poly(alkyl cyanoacrylate) such as described in WO 1999/043359, a polyamine, N-(2-hydroxypropyl) methacrylamide (HPMA), a poly(ethylene glycol), a lactic acid polymer, or a polyglutamate.

In some embodiments of the invention, R4 is represented by formula (IV) $R_5(Y)_a$ wherein Y is a spacer; a is 0 or 1; and $R_5$ is a hydrocarbon group of 3 to 30 carbon atoms, linear or branched, saturated or unsaturated, optionally substituted by one or more OH groups.

Preferably, Y is selected from the group consisting of $—(CH_2)_m—$, $—CONH(CH_2)_m—$, $—NHCO(CH_2)_m—$, $—COO(CH_2)_m—$ and $—OCO(CH_2)_m—$ with m being an integer ranging from 1 to 10.

"a is 1" means that the R4 group has a spacer so that Y is present. "a is 0" indicates that the R4 group has no spacer and Y is absent.

R5 may comprise 1, 2, 3 or 4 unsaturations which can independently be an unsaturated double or triple bond. R5 may also comprise 1, 2, 3, 4, 5 or 6 branches, said branches preferably being a methyl group.

In some embodiments, R5 is selected from the group consisting of:
(i) a $C_2$-$C_9$ alkyl optionally substituted by a hydroxyl;
(ii) a $C_2$-$C_9$ alkene, preferably of formula $—H_2C=CH(CH_2)_m—$ with n an integer ranging from 1 to 8; and
(iii) a hydrocarbon group comprising one or more moieties derived from isoprene, preferably selected from the group consisting of:
(a) $(CH_3)_2C=CH—CH_2—CH_2—[C(CH_3)=CH—CH_2—CH_2]_m—$ with m an integer ranging from 0 to 5 and
(b) $(CH_3)_2C=CH—CH_2—CH_2—[C(CH_3)=CH—CH_2—CH_2]_p—[CH=C(CH)_3—CH_2—CH_2]_q—$ with p an integer ranging from 1 to 5 and q an integer ranging from 1 to 5.

The double bond or bonds present in the R5 group can independently be in cis or trans configuration. In some embodiments, the double bond or bonds are trans.

Specific examples of compounds of the invention for which R5 corresponds to the groups defined in point (i) or (ii) have been presented above (see individual compounds 36, 38 and 40). In some embodiments of the compound according to the invention, R4 is represented by formula $R5(Y)_a$ wherein:
R5 is selected from the group consisting of:
(a) $(CH_3)_2C=CH—CH_2—CH_2—[C(CH_3)=CH—CH_2—CH_2]_m—$ with m an integer ranging from 0 to 5 and
(b) $(CH_3)_2C=CH—CH_2—CH_2—[C(CH_3)=CH—CH_2—CH_2]_p—[CH=C(CH)_3—CH_2—CH_2]_q—$ with p an integer ranging from 1 to 5 and q an integer ranging from 1 to 5;

Y is selected from the group consisting of $—(CH_2)_m—$, $—CONH(CH_2)_m—$, $NHCO(CH_2)_m—$, $—COO(CH_2)_m—$ and $—OCO(CH_2)_m—$ with m an integer ranging from 1 to 10; and
a is 0 or 1.

In some particular embodiments, R5 is a group selected from the group consisting of:
$(CH_3)_2C=CH—CH_2—CH_2-[C(CH_3)=CH—CH_2—CH_2]_2—[CH=C(CH)_3—CH_2—CH_2]_2—$,
$(CH_3)_2C=CH—CH_2—CH_2—[C(CH_3)=CH—CH_2—CH_2]_2—[CH=C(CH)_3—CH_2—CH_2]—$; and
$(CH_3)_2C=CH—CH_2—CH_2—[C(CH_3)=CH—CH_2—CH_2]_2—$.

In a preferred embodiment of the invention, R4 is a squalenoyl group, optionally comprising a spacer. According to the invention, a squalenoyl group is a group comprising the moiety: $(CH_3)_2C=CH—CH_2—CH_2—[C(CH_3)=CH—CH_2—CH_2]_2—[CH=C(CH)_3—CH_2—CH_2]_2—$. In a particular embodiment, R4 is a squalenoyl group of the following formula:

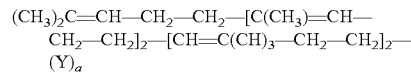

wherein Y and a are as defined above.

In a particular embodiment of the method described above, the compound R4-XH is tris-nor-squalenol, also referred to herein as squalenol, which means R4-XH is a compound of formula R5-Y—H wherein:
R5 is $(CH_3)_2C=CH—CH_2—CH_2—[C(CH_3)=CH—CH_2—CH_2]_2—[CH=C(CH)_3—CH_2—CH_2]_2—$, Y is $CH_2$ and X is O.

In another particular embodiment, the compound R4-XH is a squalenoyl group which is linked to $—C(O)NH—(CH_2)_2—SH$ (that is to say the compound: $(CH_3)_2C=CH—CH_2—CH_2—[C(CH_3)=CH—CH_2—CH_2]_2—[CH=C(CH)_3—CH_2—CH_2]_2—C(O)NH—(CH_2)_2—SH)$.

Particularly preferred compounds of formula (I) are the following:
R1 and R2 are independently H, $—CH(CH_3)—CH_2—Cl$ or $—(CH_2)_2—Cl$, provided that at least one of the two is $—CH(CH_3)—CH_2—Cl$ or $—(CH_2)_2—Cl$;
R3 is $—CH(CH_3)—CH_2—Cl$ or $—(CH_2)_2—Cl$; and,
X is O and R4 is a squalenoyl group; or R4X is squalenoyl-C(O)NH—$(CH_2)_2$—S—.

In a more preferred embodiment, R2 is H and R1 and R3 are independently selected from $—CH(CH_3)—CH_2—Cl$ and $—(CH_2)_2—Cl$. More specifically, R2 is H and R1 and R3 are $—(CH_2)_2—Cl$. Alternatively, R2 can be H and R1 and R3 are $—CH(CH_3)—CH_2—Cl$.

Specific compounds of the invention are the following:

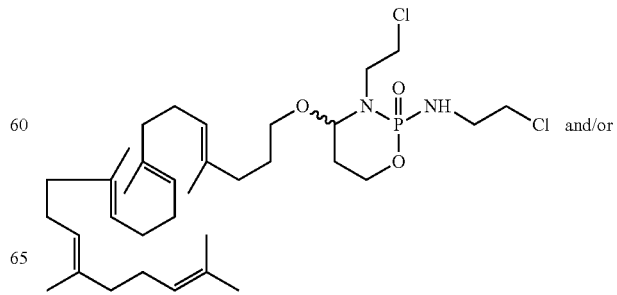

and/or

-continued

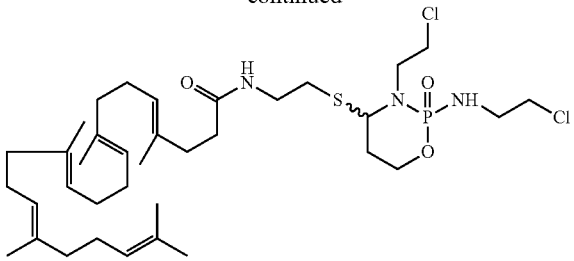

"About" is intended to mean more or less 10%, preferably more or less 5%.

When R4 is selected in such a way that it is a group, in particular a lipid group, allowing the formation of nanoparticles, micelles or liposomes, the present invention also relates to a nanoparticle formed by the compound of formula (I) of the present invention. In a preferred embodiment of the invention, R4 is a squalenoyl group, that is to say a group comprising the following moiety: $(CH_3)_2C=CH-CH_2-CH_2-[C(CH_3)=CH-CH_2-CH_2]_2-[CH=C(CH)_3-CH_2-CH_2]_2$.

More specifically, R2 is H and R1 and R3 are —$(CH_2)_2$—Cl and R4 is squalenoyl, X may be O or S. Alternatively, the compound of formula (I) can have R2 being H and R1 and R3 being —$CH(CH_3)$—$CH_2$—Cl and R4 is squalenoyl, X may be O or S. In one particularly preferred embodiment, the compounds are selected from compounds comprising a squalenoyl group as described above. The nanoparticles of compound of formula (I) can be obtained by dissolving the compound in an organic solvent such as acetone or ethanol, then adding this mixture into an aqueous phase under stirring leading to the formation of nanoparticles with or without surfactant(s). Surfactants include, for example, polyoxyethylene-polyoxypropylene copolymers, phospholipid derivatives and lipophilic derivatives of polyethylene glycol. Preferably, the nanoparticles have average sizes ranging from 30-500 nm or 70-200 nm.

The compound can be used in the form of any pharmaceutically acceptable salt. Non-limiting examples of pharmaceutically acceptable salts include pharmaceutically acceptable acid or base addition salts, hydrates, esters, solvates. The term pharmaceutically acceptable salts refers to non-toxic salts, which can generally be prepared by reacting a free base with a suitable organic or inorganic acid. These salts retain the biological effectiveness and properties of the free bases. As representative examples of such salts, one may cite water-soluble and water-insoluble salts, such as acetates, N-methylglucamine ammonium, ansonates (4,4-diaminostilbenes-2, 2'-disulfonates), benzenesulfonates, benzonates, bicarbonates, bisulfates, bitartrates, borates, hydrobromides, bromides, buryrates, camsylates, carbonates, hydrochlorides, chlorides, citrates, clavulariates, dihydrochlorides, diphosphates, edetates, calcium edetates, edisylates, estolates, esylates, fumarates, gluceptates, gluconates, glutamates, glycolylarsanylates, hexafluorophosphates, hexylresorcinates, hydrabamines, hydroxynaphthoates, iodides, isothionates, lactates, lactobionates, laurates, malates, maleates, mandelates, mesylates, methylbromides, methylnitrates, methylsulfates, mucates, napsylates, nitrates, 3-hydroxy-2-naphthoates, oleates, oxalates, palmitates, pamoates (1,1-methylene-bis-2-hydroxy-3-naphthoates, or emboates), pantothenates, phosphates, picrates, polygalacturonates, propionates, p-toluenesulfonates, salicylates, stearates, subacetates, succinates, sulfates, sulfosalicylates, suramates, tannates, tartrates, teoclates, tosylates, triethiodides, trifluoroacetates, or valerates.

The present invention also relates to a pharmaceutical composition comprising an oxazaphosphorine derivative of formula (I) or a nanoparticle such as defined above. The pharmaceutical composition can advantageously include a pharmaceutically acceptable carrier or excipient. The pharmaceutically acceptable carrier can be selected from conventionally used carriers according to each of mode of administration. Depending on the intended mode of administration, the compounds may be in solid, semi-solid or liquid form. For solid compositions such as tablets, pills, powders or granules in the free state or contained in capsules, the active substance can be combined with: a) diluents, for example lactose, dextrose, sucrose, mannitol, sorbitol, cellulose and/or glycine, b) lubricants, for example silica, talc, stearic acid, its magnesium salt or calcium salt and/or polyethylene glycol, c) binders, for example magnesium and aluminum silicate, starch paste, gelatin, tragacanth, methylcellulose, sodium carboxymethylcellulose and/or polyvinylpyrrolidone, d) disintegrating agents, for example starch, agar, alginic acid or its sodium salt, or effervescent mixtures; and/or e) absorbents, coloring agents, flavoring agents and sweeteners. Excipients may be, for example, mannitol, lactose, starch, magnesium stearate, sodium saccharin, talc, cellulose, glucose, sucrose, magnesium carbonate and analogues of pharmaceutical grade. For semi-solid compositions such as suppositories, the excipient may be, for example, an emulsion or oily suspension, or polyalkylene glycol, such as polypropylene glycol. Liquid compositions, particularly injectable ones or those to be included in a soft capsule, can be prepared for example by dissolving, dispersing, etc. the active substance in a pharmaceutically pure solvent such as, for example, water, physiological saline solution, aqueous dextrose, glycerol, ethanol, oils and the like.

The composition may further comprise another active ingredient. In a particular embodiment, the additional active agent is an anticancer agent. Non-limiting examples include in particular interferons, cisplatin, bleomycin, fluorouracil, methotrexate, vincristine, actinomycin, vinorelbine, taxanes such as paclitaxel and docetaxel, or an anthracycline. Furthermore, an active ingredient for counteracting the toxicity of oxazaphosphorines can be added to the pharmaceutical composition, in particular sodium mercaptoethanesulfonate. The pharmaceutical composition may also be used in combination with radiotherapy.

The composition of the invention can be administered by any suitable route, and, without being limited to, the parenteral route, for example as injectable preparations by the subcutaneous, intramuscular or intravenous route; by the oral route (per os), for example in the form of coated or uncoated tablets, capsules, powders, granules, oral solutions or suspensions (such form for oral administration may be either immediate release or sustained or delayed release); by the rectal route, for example in the form of suppositories; —topically, in particular transdermally, for example in the form of patches, ointments or gels; —intranasally, for example in the form of aerosols and sprays; —under the tongue; —intraocularly.

The pharmaceutical composition typically comprises an effective dose of an oxazaphosphorine derivative of formula (I) of the invention. A "therapeutically effective dose" as described here is understood to mean the dose that produces a therapeutic effect for a given condition and administration regimen. This is typically the average dose of an active substance to be administered to significantly improve some of the symptoms associated with a disease or a pathological state.

A "therapeutically effective dose" of an active substance does not have to cure a disease or disorder but will provide a treatment for this disease or disorder so that its onset is delayed, hindered or prevented, or its symptoms are attenuated, or its course is modified or, for example, is less severe or the patient's recovery is accelerated. It is understood that the "therapeutically effective dose" for a particular person depends on various factors, including activity/efficacy of the active substance, time of administration, route of administration, its rate of excretion and metabolism, drug combinations/interactions, and the severity of the disease (or disorder) treated preventively or curatively, as well as age, body weight, overall health, gender and/or the patient's diet.

For systemic treatment, it is conceivable to administer the compound of formula (I) at a dose of approximately 25 to 500 mg/kg body weight per day, preferably approximately 25 to 300 mg/kg.

The present invention also relates to a pharmaceutical composition according to the invention for use in the treatment of cancer or as immunosuppressant. It also relates to the use of a pharmaceutical composition according to the invention, an oxazaphosphorine derivative of formula (I) or a nanoparticle such as defined above for the manufacture of a medicament for the treatment of cancer or that of an immunosuppressant. Finally, the present invention relates to a method for treating a subject having a cancer, the method comprising administering a therapeutically effective dose of a pharmaceutical composition according to the invention, of an oxazaphosphorine derivative of formula (I) or a nanoparticle such as defined above. The present invention also relates to a method for treating a subject in need of immunosuppression, the method comprising administering a therapeutically effective dose of a pharmaceutical composition according to the invention, that of an oxazaphosphorine derivative of formula (I) or that of a nanoparticle such as defined above.

The cancer can be a solid tumor or a hematopoietic cancer. Thus, the cancer can be selected from the group consisting of the chronic leukemias, acute lymphocytic leukemias, Hodgkin's disease, Hodgkin's and non-Hodgkin lymphomas, cancers of the lung, breast, prostate, bladder and ovaries, sarcomas, neuroblastomas, myelomas, melanomas, etc.

Other aspects and advantages of the present invention will become apparent upon reading the following examples, which are only illustrative in nature, but do not limit the scope of this application.

EXAMPLE 1

Preparation of 4-Substituted Analogues of IFO (Ifosfamide)

The anodic oxidation of ifosfamide in methanol provides access to a chemical entity (4-MeO-IFO), whose cytotoxic potency is equivalent to that of the active metabolite of IFO. However, this 4-MeO-IFO is quite unstable from a chemical point of view, releasing isophosphoramide mustard rapidly. In order to modulate the release kinetics and facilitate intracellular penetration of this very polar small molecule, the inventors considered inserting longer aliphatic chains at this position 4. This concept is the first step toward modifying ifosfamide to insert it into a lipophilic vectorized form, such as a liposome or nanoparticle system.

Substitution By Direct Route

Oxidation of ifosfamide generates an iminium. This is trapped by the nucleophile present in the medium, leading to a 4-substituted oxazaphosphorinane. The purpose of this description is to study the feasibility of this synthetic route and to evaluate the substrates and the minimum amount compatible with this direct route.

Electrochemical Oxidation of Ifosfamide in the Presence of Pentan-1-ol:

In a first step, the inventors used primary amyl alcohol to study the feasibility of this reaction in the presence of a long chain aliphatic alcohol.

To define a procedure as efficient as possible, the inventors varied the experimental reaction conditions described in Scheme 1.

Scheme 1: Anodic oxidation of IFO in the presence of primary amyl alcohol

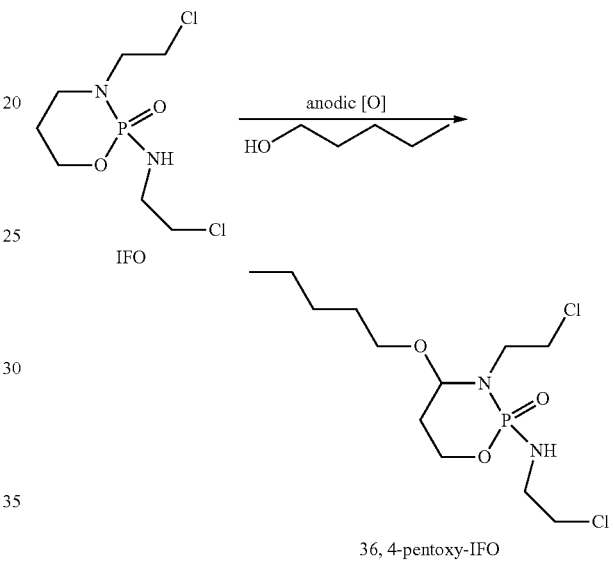

36, 4-pentoxy-IFO

Electrolysis of IFO was carried out in the presence of pentan-1-ol in acetonitrile, at constant current through the graphite electrode. Tetraethylammonium tetrafluoroborate ($TEABF_4$) was the supporting electrolyte that was used. The reaction was followed by thin layer chromatography (TLC) and stopped when all the IFO was consumed. After stopping the reaction, sodium bicarbonate was added to neutralize the electrogenerated acidity. The obtained products, which could be isolated, were then purified by column chromatography.

IFO is a racemic mixture due to the chirality conferred by the phosphorus. As for methoxylation, pentoxylation generated four diastereomers, pairwise enantiomers.

By nature, the enantiomers could not be physically differentiated. On the other hand, the $^{31}$P-NMR chemical shifts for the two pairs of diastereomers were distinct.

The proportions of the various products were therefore determined by $^{31}$P-NMR.

By analogy with methoxylation, it was possible to assign the $^1$H-NMR signals to one or the other diastereomeric forms: in fact, addition of an alkoxy group on the α carbon of the nitrogen results in a group with 3 signals corresponding to the hydrogens carried by C4 and C6, and which differ from one diastereomer to the other.

Influence of the Amount of Alcohol

The electrolysis was carried out by varying the amount of alcohol introduced. For a given quantity of supporting electrolyte (1 Eq.), the results are summarized in Table 1.

TABLE 1

Influence of the amount of nucleophile

| Test | Eq. of Pentanol | Current (mA) | Reaction stopped | Yield (%) |
|---|---|---|---|---|
| A | 9 | 20 | 3.75 F/mol | <15 |
| B | 15 | 20 | 3.60 F/mol | 34 |
| C | 30 | 20 | 3.75 F/mol | 41 |

Initially, at least 15 equivalents of alcohol appeared to be necessary to obtain a satisfactory yield (calculated with reference to IFO). On the other hand, the gain obtained when increasing from 15 to 30 equivalents was low.

Anodic Oxidation of IFO in the Presence of Different Alcohols

The aim here, using the conditions developed with pentan-1-ol, was to study the compatibility of different functional groups on the alcohol with the electrochemical process.

The general reaction is shown in Scheme 2.

Scheme 2: General alkoxylation reaction of IFO

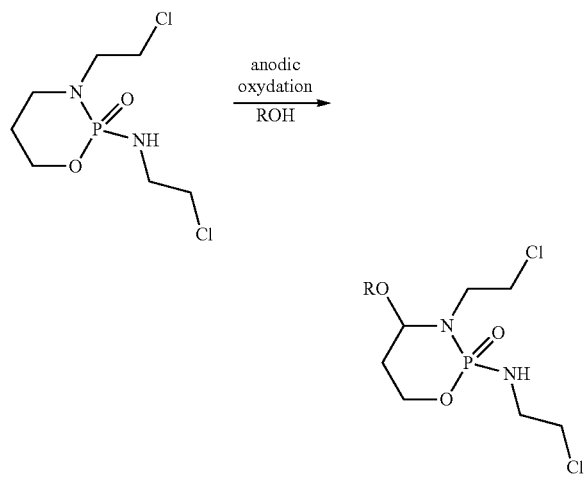

IFO therefore was electrochemically oxidized in acetonitrile in the presence of various alcohols with 5 carbon atoms. The reaction was stopped when all the starting material appeared to be consumed as monitored by TLC. At the end of the reaction, sodium bicarbonate (1 Eq.) was added to the medium to neutralize electrogenerated hydrons. The proportions of the various diastereomers were determined on the crude reaction mixture by $^{31}$P-NMR before being isolated by "flash chromatography".

The results of these operations are described in Table 2.

TABLE 2

Summary of various alkoxylation tests

| | | Results | |
|---|---|---|---|
| Alcohol | Stop (F/mol) | Proportions of diastereomers | Overall yield (%) |
| Pentan-1-ol | 3.6 | 80/20 | 34 |
| Pentan-3-ol | 2.7 | 55/45 | 0* |
| Pentan-1,2-diol | 2.5 | 52/48 | 22 |
| Pentan-1,4-diol | 3.5 | 53/47 | 0* |
| 4-Penten-1-ol | 2.9 | ND | 19 |
| Heptan-1,7-diol | 2.7 | 80/20 | 27 |

*products not isolated.

At first, it was observed that a secondary alcohol seems more difficult than a primary alcohol to attach on IFO. Indeed, the NMR spectra of the crude electrolysis showed only traces of alkoxylation. Alkoxylated products formed in small quantities could not be isolated. Steric hindrance would prevent the alcohol from accessing the iminium of IFO.

In addition, in the case of competition between a primary and secondary alcohol, the fixation was almost exclusively carried out by the primary alcohol, the rest of the chain remaining unchanged. During the tests using diols, the NMR spectra of the crude reaction mixtures revealed the presence of products compatible with the expected adducts. This was confirmed in the case of pentan-1,2-diol. However, despite a presence in the crude reaction, the products could not be purified in the case of pentan-1,4-diol.

The use of a compound having two primary alcohol functions makes it possible to reduce the number equivalents to 10 Eq. (compared to 15 used for other alcohols), while maintaining an equivalent yield. Under the conditions used, the forms attached with two alcohols were not characterized.

These results allow the possibility of selective fixation of polyols by a primary alcohol function. This was a first step toward the fixation of an ose on IFO, in the context of vectorization.

The presence of a C=C double bond did not prevent the fixation of the primary alcohol to IFO and it was not modified during the electrochemical reaction.

Compatibility of Different Functions with the Direct Oxidation Protocol

Besides using a large amount of nucleophile, the direct oxidation protocol requires the use of compounds resistant to oxidizing conditions.

Amines

Amines can be oxidized under the conditions used. Thus, in these conditions, and in the presence of ifosfamide, there is concomitant oxidation of the two compounds (IFO and amine).

Thiol

Under oxidizing conditions, thiols dimerize by forming a disulfide bridge (Scheme 3).

Scheme 3: Dimerization of thiol under oxidizing conditions.

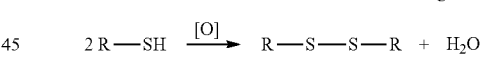

The nucleophilic center (sulfur atom) is no longer available for substitution on the iminium.

Conclusions and Prospects

The anodic oxidation protocol of IFO in the presence of 15 equivalents of alcohol is possible. It allows simple access to novel compounds, never described. This protocol is also applicable to other oxazaphosphorines such as cyclophosphamide and trofosfamide. To optimize this reaction, it is necessary to use an anhydrous reaction medium, in order to eliminate a competitor nucleophile.

However, the disadvantages of this direct route are manifold.

The need to use 15 Eq of nucleophile poses several problems: this method is limited to inexpensive reagents, and this excess reagent impedes the purification of sensitive products. Lastly, the use of nucleophilic compounds with oxidizable functions is impossible.

Substitution by Indirect Route

Iminium Trapped then Regenerated

This protocol consists of 3 stages:
anodic methoxylation,
amidoalkylation, broken down into
  regeneration of the iminium then
  in situ reaction with the nucleophile.

This 3-stage reaction sequence is carried out in 2 reaction media (Scheme 4).

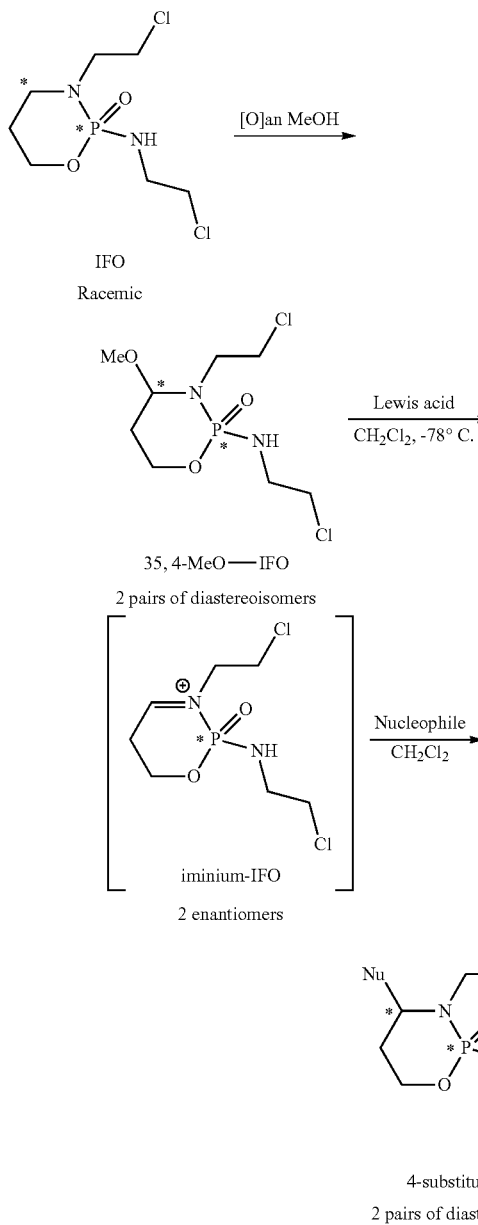

Scheme 4: Reaction sequence via 4-MeO—IFO

In practice, ifosfamide undergoes electrolysis in methanol, then the 4-MeO-IFO derivative is brought into contact with a Lewis acid in a non-nucleophilic solvent to regenerate the iminium with which the nucleophile reacts.

This technique allows the use of nucleophiles incompatible with anodic oxidation. Compared with the direct route, the other advantage of this technique is the use of a smaller number of nucleophile equivalents.

The iminium was electrogenerated by anodic oxidation in methanol and therefore trapped in the form of 4-MeO-IFO.

Once ifosfamide was totally consumed (passage of more than 2.5-3.0 F/mol), the solvent was evaporated in the presence of a base, sodium carbonate ($Na_2CO_3$), to prevent acidification of the medium. The residue was taken up in diethyl ether followed by simple filtration to give access to the methoxylated products. When a bit of starting material remains, or if the separation of the diastereomers is desired, a chromatographic column is required.

Finally, many methoxylations on different amounts of IFO, ranging from a few dozen milligrams to a few grams, were carried out. In a 15 mL electrochemical cell, oxidation of 2 grams of IFO was carried out, for example. Methoxylated derivatives were obtained with a yield of 82% (1.8 g), after passage of 4.0 F. $mol^{-1}$. Thus this electrochemical reaction seems appropriate to use for synthesis: it is fairly simple to implement even though the purification requires a certain know-how. Moreover, the products obtained are relatively stable and can be stored for several weeks in a freezer under an inert atmosphere.

Under the action of a Lewis acid, the methoxyl group can regenerate iminium which will be trapped by a variety of nucleophiles to give access to various structures. Amidoalkylation is the reaction consisting of regenerating the iminium ion from the methoxylated derivative then carrying out a nucleophilic addition on this iminium.

Regeneration of the iminium intermediate from the methoxylated derivative occurs through the use of a Lewis acid. The most conventionally used Lewis acids include: $BF_3.OEt_2$, $TiCl_4$, $Yb(OTf)_2$, TMSOTf.

The Lewis acid is merely involved in the regeneration of the iminium from the methoxylated derivative and not in the diastereoselectivity of the addition.

Electrolysis—Methoxylation by Anodic Oxidation

Angelo Paci and Thierry Martens described the anodic oxidation of IFO and CPM in a single-compartment cell (Paci et al. 2001b) (Scheme 5).

Scheme 5: Electrochemical 4-methoxylation of IFO

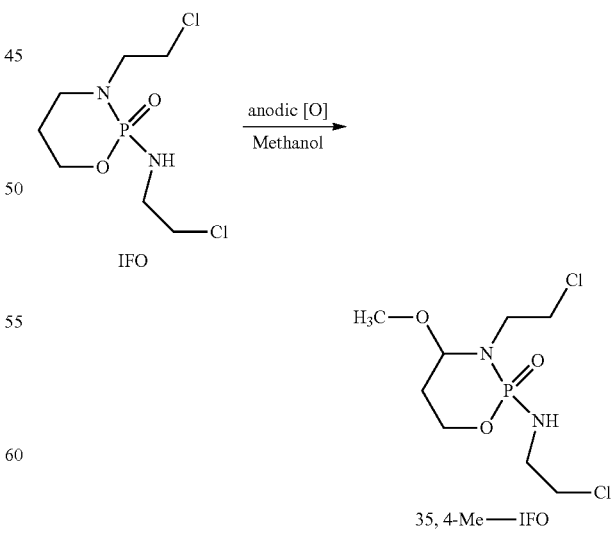

To obtain a known end product, the study focused on the following sequence using pentan-1-ol as nucleophile (Scheme 6).

17

Scheme 6: Amidoalkylation sequence

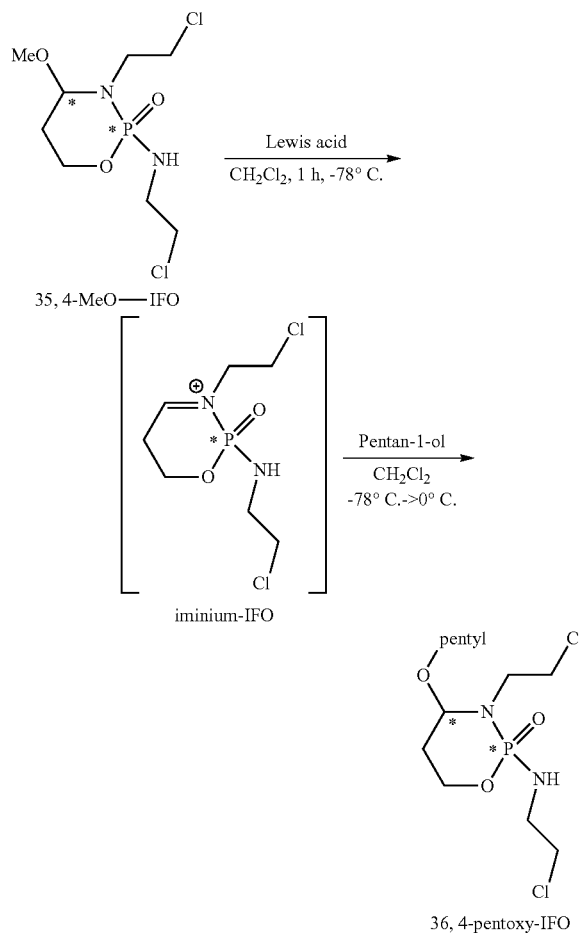

4-MeO-IFO was contacted with a Lewis acid at low temperature (−78° C.) for 1 hour (arbitrarily). The nucleophile (1 Eq. of amyl alcohol) was then added to the mixture which was placed at 0° C. for 15 minutes. As the pentoxy-IFO have already been identified, a simple $^{31}$P-NMR spectrum allowed rapid determination of reaction efficiency, as summarized in Table 3.

TABLE 3

Influence of the Lewis acid used in the amidoalkylation

| Lewis acid | | Results | |
|---|---|---|---|
| Nature | Quantity (Eq) | Conversion (%) | Proportion dias (9.6/9.3 ppm) |
| TMSOTf | 0.1 | 30 (+ degradation) | 85/15 |
|  | 0.5 | Degradation | ND |
|  | 1 | Degradation | ND |
| Ti(OEt)$_4$ | 0.1 | 0% | Remaining 4-MeO-IFO & degradation products |
|  | 0.5 | 0% |  |
|  | 1 | 0% |  |
| BF$_3$•OEt$_2$ | 0.1 | 59 | 82/18 |
|  | 0.5 | 48 | 80/20 |
|  | 1 | Degradation | ND |

It appears that the Ti (OEt)$_4$ is not reactive enough to regenerate iminium from 4-MeO-IFO. Furthermore, TMSOTf appears to induce degradation of 4-MeO-IFO, except when used in catalytic amounts (10 mol %), which leads to the formation of diastereomers with a poor yield. The Lewis acid used does not seem to affect the diastereoselectivity of the reaction, but rather influences the yield and stability of the intermediate iminium generated, contributing to the purity of the crude reaction. In this study, it was found that the boron trifluoride etherate used in catalytic amounts (BF$_3$OEt$_2$) was the most effective Lewis acid tested.

The conditions (0.1 Eq. BF$_3$.OEt$_2$, 1 hour at −78° C. in CH$_2$Cl$_2$) identified above were subsequently used to evaluate the influence of the amount of pentan-1-ol on the conversion. The results are summarized in Table 4.

18

TABLE 4

Influence of reaction time of the iminium

| Pentan-1-ol | | Results | |
|---|---|---|---|
| Quantity (Eq.) | Time (min) | Conversion (%) | Proportion dias (9.6/9.3 ppm) |
| 1 | 15 | 59 | 82/18 |
| 2 | 15 | 60 | 81/19 |
| 2 | 30 | 64 | 85.4/14.6 |
| 2 | 45 | 62 | 83.5/16.5 |
| 2 | 120 | 61 | 82/18 |

The amount of pentan-1-ol does not seem to influence the conversion rate or the proportion of diastereomers formed. Despite comparable levels of conversion, it seems that the optimum reaction time is half an hour, with a conversion of 64% and a diastereomer ratio of 85.4/14.6.

In some experiments, the inventors verified that the use of THF in place of dichloromethane did not modify the results observed.

Competitors nucleophiles are methanol generated at the same time as the iminium and residual water present in the medium. The inventors have attempted to add activated 4 A molecular sieves to sequester residual water and released methanol. This addition did not appear to significantly improve the observed yields.

Conjugation of other substrates such as amines, poly functionalized compounds or lipids is possible, and has been envisioned to allow the formation of pre-activated IFO analogues targeted and vectorized to tumors by attaching fatty acids or other lipids, a peptide or a sugar.

For example, the most recent and most promising application concerns the attachment of a squalene residue by this method by adding squalenol or squalene-thiol in the presence of BF$_3$,ET$_2$O on the phosphoryl-iminium produced from 4-methoxy-MFI (Scheme 7 and 8). The compounds formed, SQ-4-O-MFI and SQ-4-S-MFI, have two interesting properties. The first is that they are pre-activated forms of MFI due to oxidation in position 4 that can release, in slightly acidic aqueous medium, the alkylating mustard directly without metabolic activation. The second is that they are capable of self-assembly in aqueous medium in the form of nanoparticles of a size of about 160 nm.

Scheme 7: Amidoalkylation using squalenol

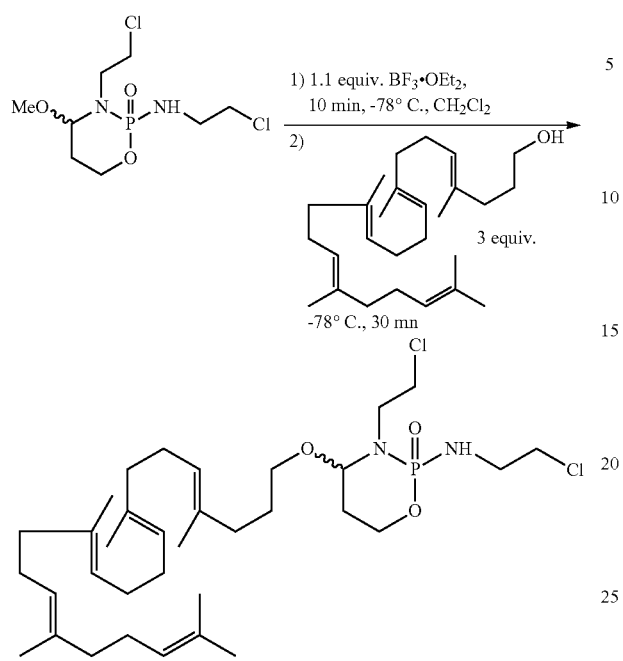

tage of this technique is the use of small amounts of nucleophiles. This will be a major advantage when using expensive nucleophiles. Moreover, this technique is compatible with a wider variety of nucleophiles. Finally, the production of 4-MeO-IFO is feasible on large amounts of IFO.

Structural Analysis (2-chloro-ethyl)-[3-(2-chloro-ethyl)-2-oxo-4-pentyloxy-2λ5-[1,3,2]oxazaphosphinan-2-yl]-amine or 4-pentoxy-IFO

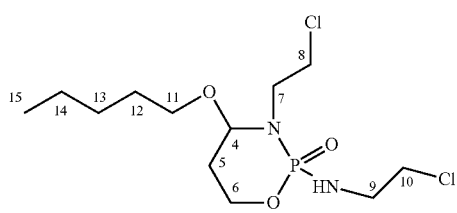

36a et 36b

Protocol: In an 8 mL electrochemical cell, 110 mg IFO (0.4 mmol) were dissolved in 4.0 mL of anhydrous acetonitrile.

Scheme 8: Amidoalkylation using squalenol with thionyl spacer (cysteamine)

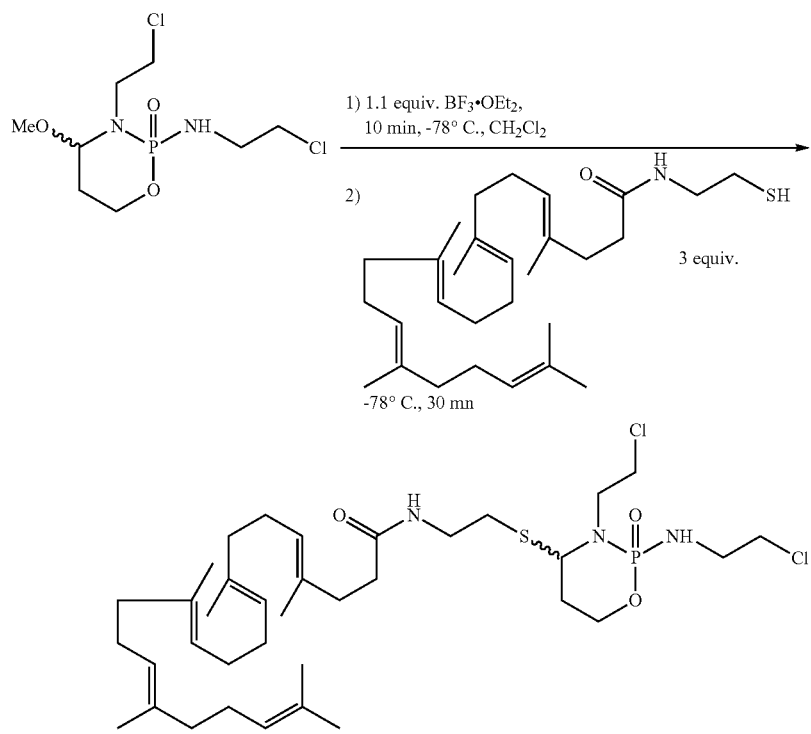

The same type of reaction was considered for cyclophosphamide or trofosfamide which can also be oxidized at position 4 in the 4-methoxy form to lead to the phosphoryl imine form.

This two-stage method produces 4-substituted analogues of ifosfamide. Compared to direct oxidation, the main advan- One equivalent of a supporting electrolyte (95 mg tetraethylammonium tetrafluoroborate) then fifteen equivalents (7.1 mmol, 0.77 mL) of pentan-1-ol were added. The mixture was degassed by bubbling nitrogen and placed in an ice bath. Agitation was provided by a magnetic stirrer. Two electrodes were introduced into the cell.

After the passage of 3.6 F/mol at 20 mA, the reaction was stopped by turning off the electric current. One equivalent of sodium bicarbonate was added to the medium to neutralize hydrons released during the reaction, which may degrade the product.

The solvent was evaporated under reduced pressure, and the residue was taken up twice in 8 mL of acetonitrile to eliminate the maximum of alcohol. 15 mL of ethyl ether were then added to insolubilize the supporting electrolyte. After filtration of the ether phase, it was evaporated under reduced pressure.

The resulting products were purified by chromatography (eluent ethyl ether/methanol; 95/5). Diastereomers 36a and 36b were obtained with 90% separation.

Organoleptic character: slightly yellow oil

Rf=0.24 and 0.39 for X1 and X2 (Et$_2$O).

Molecular formula: $C_{12}H_{25}Cl_2N_2O_3P$

NMR in CDCl$_3$ $^{31}$P δ (ppm): 9.6 (diastereomer 36a), 9.3 (diastereomer 36b).

$^{13}$C δ (ppm): 13.9 ($C_{15}$); 22.4 ($C_{14}$); 28.4 ($C_{13}$); 29.5 ($C_5$); 42.7 ($C_7$); 44.0 ($C_8$); 46.6 ($C_{10}$); 49.5 ($C_9$); 62.5 ($C_{11}$); 68.5 ($C_6$); 89.3 ($C_4$).

$^1$H δ (ppm): 0.92 (t, 3H, $H_{15}$); 1.40 (m, 4H, $H_{13}$, $H_{14}$); 1.62 (m, 2H, $H_{12}$); 2.10 (m, 1H, $H_{5\ Eq.}$); 2.26 (td, 1H, $H_{5\ Ax.}$); 3.33 (m, 2H, $H_9$); 3.45 (m, 2H, $H_7$); 3.56 (m, 2H, $H_{11}$); 3.73 (m, 4H, $H_{10}$, $H_8$); 4.15 (m, 1H, $H_{6\ Eq.}$); 4.45 (m, 1H, $H_{6\ Ax.}$); 4.60 (m, 1H, $H_4$).

1-[3-(2-chloro-ethyl)-2-(2-chloro-ethylamino)-2-oxo-2λ$^5$-[1,3,2]oxazaphosphinan-4-yloxy]-pentan-2-ol or 4-(2OH)-pentoxy-IFO

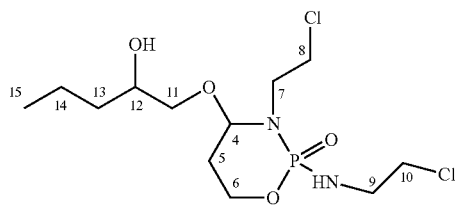

38

Protocol similar to that used for 4-pentoxy-IFO

The resulting products were purified by chromatography (eluent ethyl ether/methanol; 90/10), 2 successive columns.

Organoleptic character: slightly yellow oil.

Rf=0.32 and 0.50 for X1 and X2 respectively (hardly distinguishable spots) (Et$_2$O/MeOH 90/10).

Molecular formula: $C_{12}H_{25}Cl_2N_2O_4$.

NMR in CDCl$_3$.

$^{31}$P δ (ppm): 9.78 (diastereomer 38a), 9.88 (diastereomer 38b).

$^1$H δ (ppm): 0.95 (t, 3H, $H_{15}$); 1.30 (bs, 1H, OH); 1.40 (m, 4H, 2H$_{13}$, 2H$_{14}$); 1.92 (m, 2H, $H_5$); 2.25 (bs, 1H, NH); 3.30 (m, 4H, 2H$_7$, 2H$_9$); 3.40 (m, 3H, 2H$_{11}$, $H_{12}$); 3.70 (m, 4H, 2H$_8$, 2H$_{10}$); 4.15 (m, 1H, $H_{6Eq.}$); 4.50 (m, 1H, $H_{6Ax.}$); 4.70 (m, 1H, $H_4$).

(2-chloro-ethyl)-[3-(2-chloro-ethyl)-2-oxo-4-pent-4-enyloxy-2λ$^5$-[1,3,2]oxazaphosphinan-2-yl]-amine or 4-pentenoxy-IFO

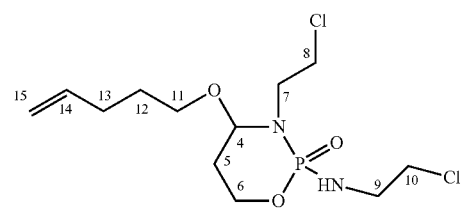

40

Protocol similar to that used for 4-pentoxy-IFO

The resulting products were purified by chromatography (eluent ethyl ether/methanol; 97/3).

Organoleptic character: slightly yellow oil.

Rf=0.68 and 0.78 for X1 and X2 respectively (hardly distinguishable spots) (Et$_2$O/MeOH 95/5).

Molecular formula: $C_{12}H_{23}Cl_2N_2O_3$.

IR (film); ν (cm$^{-1}$): 2924 (C—H), 2361, 1640 (C=C), 1434 (P—N), 1257 (P=O), 1065-1113 (P—O—C).

NMR in CDCl$_3$.

$^{31}$P δ (ppm): 9.51 (diastereomer 40a), 9.23 (diastereomer 40b).

$^{13}$C δ (ppm): 28.9 ($C_5$); 35.6 ($C_{12}$); 36.9 ($C_{13}$); 42.6 ($C_9$); 44.5 ($C_7$); 47.3 ($C_8$); 50.0 ($C_{10}$); 62.5 ($C_6$); 67.8 ($C_{11}$); 89.5 ($C_4$); 115.9 ($C_{15}$); 138.0 ($C_{14}$).

$^1$H δ (ppm): 0.95 (bs, 1H, NH); 1.30 (m, 2H, 2H$_{13}$); 1.48 (s, 1H, 1H$_{11}$); 1.75 (q, 2H, $H_{12}$); 1.90 (d, 1H, $H_{11'}$); 2.25 (m, 2H, 2H$_5$); 3.20 (m, 2H, 2H$_9$); 3.35 (m, 2H, 2H$_7$); 3.65 (m, 2H, 2H$_8$); 3.75 (m, 2H, 2H$_{10}$); 4.25 (m, 1H, $H_{6Eq.}$); 4.50 (m, 1H, $H_{6Ax.}$); 4.65 (m, 1H, $H_4$); 5.10 (m, 2H, 2H$_{15}$); 5.80 (m, 1H, $H_{14}$).

(2-chloro-ethyl)-[3-(2-chloro-ethyl)-2-oxo-4-squalenyl-[1,3,2]oxazaphosphinan-2-yl]-amine or 4-SQ-IFO

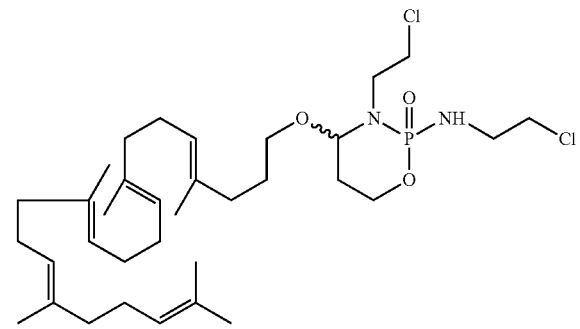 [SMILES: CC(C)=CCC/C(C)=C/CC/C(C)=C/CC/C=C(\C)CC/C=C(\C)CCCOC1CCOP(=O)(NCCCl)N1CCCl]

Protocol: From 4-methoxy-ifosfamide, under similar conditions to the previous products (−78° C., CH$_2$Cl$_2$, BF$_3$, EtO$_2$, 30 min), 1 equivalent of tris-nor-squalenol was added to form the desired compound with a yield of 53%.

The resulting products were purified by chromatography.

Organoleptic characters: slightly yellow oil.

Molecular formula: $C_{34}H_{61}Cl_2N_2O_3P$

IR (film); ν (cm$^{-1}$): 2956 (C—H), 2352, 1638 (C=C), 1432 (P—N), 1258 (P=O), 1063-1109 (P—O—C).

NMR in CDCl$_3$.

$^{13}$C δ (ppm): 33.4 (C$_5$); 35.6 (C$_{12}$); 36.9 (C$_{13}$); 42.6 (C$_9$); 44.5 (C$_7$); 47.3 (C$_8$); 50.0 (C$_{10}$); 63.5 (C$_6$); 67.8 (C$_{11}$); 89.5 (C$_4$); 125.9 (C$_{ethylen.}$); 132.0 (C$_{quant.}$).

$^1$H δ (ppm): 0.95 (bs, 1H, NH); 1.30 (m, 2H, 2H$_{13}$); 1.55 (s, 18H); 1.95 (m, 20H); 3.20 (m, 2H, 2H$_9$); 3.35 (m, 2H, 2H$_7$); 3.55 (m, 2H, 2H$_8$); 3.65 (m, 2H, 2H$_{10}$); 4.25 (m, 1H, H$_{6Eq.}$); 4.50 (m, 1H, H$_{6Ax.}$); 4.65 (m, 1H, H$_4$); 5.05 (m, 5H, H$_{ethylen}$).

(2-chloro-ethyl)-[3-(2-chloro-ethyl)-2-oxo-4-mer-captoethylamidosqualen-[1,3,2]oxazaphosphinan-2-yl]-amine or 4-thio SQ-IFO

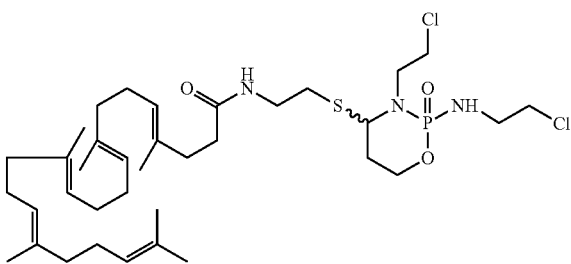 [SMILES: CC(C)=CCC/C(C)=C/CC/C(C)=C/CC/C=C(\C)CC/C=C(\C)CCC(=O)NCCSC1CCOP(=O)(NCCCl)N1CCCl]

Protocol: From 4-methoxy-ifosfamide, under similar conditions to the previous products (−78° C., CH$_2$Cl$_2$, BF$_3$, EtO$_2$, 30 min), 1 equivalent of cysteamido-squalenic acid was added to form the desired compound with a yield of 60%.

The resulting products were purified by chromatography.

Organoleptic characters: slightly yellow oil.

Molecular formula: C$_{36}$H$_{64}$Cl$_2$N$_3$O$_3$PS

IR (film); ν (cm$^{-1}$): 2956 (C—H), 2352, 1746, (C=O), 1638 (C=C), 1432 (P—N), 1258 (P=O), 1063-1109 (P—O—C)

NMR in CDCl$_3$.

$^{13}$C δ (ppm): 33.4 (C$_5$); 35.6 (C$_{12}$); 36.9 (C$_{13}$); 42.6 (C$_9$); 44.5 (C$_7$); 47.3 (C$_8$); 50.0 (C$_{10}$); 63.5 (C$_6$); 67.8 (C$_{11}$); 89.5 (C$_4$); 125.9 (C$_{ethylen.}$); 132.0 (C$_{quant.}$).

$^1$H δ (ppm): 0.95 (bs, 1H, NH); 1.30 (m, 2H, 2H$_{13}$); 1.55 (s, 18H); 1.95 (m, 20H); 3.20 (m, 2H, 2H$_9$); 3.35 (m, 2H, 2H$_7$); 3.55 (m, 2H, 2H$_8$); 3.65 (m, 2H, 2H$_{10}$); 4.25 (m, 1H, H$_{6Eq.}$); 4.50 (m, 1H, H$_{6Ax.}$); 4.65 (m, 1H, H$_4$); 5.05 (m, 5H, H$_{ethylen}$), 7.35 (bs, 1H, NH).

Note: cysteamido-squalene acid and tris-nor squalenol can be obtained from squalene aldehyde by conventional synthetic methods. The synthesis of aldehyde derivatives of squalene is described in Ceruti et al. J. Chem. Soc, Perkin Trans. 1, 2002, 1477-1486 (see FIG. 2 p. 1479).

EXAMPLE 2

Biological Evaluation of Compounds 4-Thio SQ-IFO and 4-SQ-IFO

I. Evaluation of In Vitro Cytotoxicity

I.1. Materials and Methods:
Cell Culture and Culture Conditions

Cytotoxicity of SQ-IFO and SQ-thio-IFO nanoparticles was studied in several cell lines:

A549: human alveolar basal epithelial cell adenocarcinoma
MCF-7: human breast carcinoma
MCF-7 MDR: multidrug resistant human breast carcinoma
B16F10: mouse melanoma
KB 3.1: human epidermoid carcinoma
M109: mouse lung tumor cells
MiaPaCa-2: human pancreatic carcinoma
UW-479: human pediatric glioma
IGR OV1: human ovarian cancer
SK-N-MC: neuroblastoma, reclassified as Ewing (expression of EWS/Flip-1oncogene)

The cell lines were maintained in DMEM or RPMI medium supplemented with 10% fetal calf serum and 1% antibiotics (100 U/mL penicillin and 100 μg/mL streptomycin) in an incubator at 37° C. in a humid 5% carbon dioxide atmosphere.

The cells were seeded in 96-well plates (TPP). Seeding was optimized for each line for an incubation time of 72 hours.

A549, MCF-7, B16F10, M109, MiaPaCa-2 cells were seeded at $5.10^3$ cells/well. KB 1.3 cells were seeded at $2.10^3$ cells/well, IGR-OV1 cells at $10^4$ cells/well and UW479 and SK-N-MC cells at $5.10^4$ cells/well.

Preparation of Nanoparticle Suspensions

The compounds SQ-IFO and SQ-thio-IFO were synthesized according to the protocol described above. For each compound, an aqueous suspension of nanoparticles was prepared using the technique described by Fessi, Int. J. Pharm, 1989, 55, R1-R4. The nanoparticles obtained are spherical and have an average size of 182 nm.

For each compound, different concentrations between 0.1 and 100 μM were tested by serial dilution of a 2 mg/mL stock solution for SQ-IFO and a 10 mg/mL stock solution for SQ-thio-IFO in culture medium.

Cell Viability Test

After 72 hours of incubation, cell viability was determined by observing the reduction of MTS reagent to formazan (Kit Cell titer 96 Aquerus one solution, Promega). 20 μL of a 5 mg/mL solution of MTS in PBS were added per well. The incubation time of the MTS was optimized for each cell line; the absorbance at 490 nm was then read using a plate reader (EL808, Biotek).

The results are expressed as percentage of untreated cells. The data were treated with Prism 4 software (Graph Pad Software, San Diego). IC50 values were thus calculated for each line. Ifosfamide and squalenol were used as controls.

I.2. Results

Table 5 below shows, for each compound tested, the IC50 obtained for each cell line.

It is clear that the compounds IFO-SQ and IFO-thio-SQ exhibit high in vitro cytotoxicity: these compounds are thus capable of releasing the alkylating mustard without prior activation by cytochrome P450.

Remarkably, a different activity profile was observed for IFO-thio- and IFO-SQ depending on the cancer cell line. IFO-thio-SQ had high cytotoxic activity on M109 cell lines, SK-N-MC (Ewing), UW 479 (glioma) and IGR-OV1 (Ovary) cells. Such activity was not observed for the compound IFO-SQ.

Squalenol and IFO did not exhibit significant cytotoxicity at the concentrations tested.

TABLE 5

IC50 of IFO, IFO-SQ and IFO-thio-SQ on each cell line tested.

| IC50 (μM) | Ifosfamide | Ifosfamide SQ | Ifosfamide-thio-SQ |
|---|---|---|---|
| A549 | >100 | 32.5 | 5.3 |
| MCF-7 | >100 | 43.6 | 10.9 |
| MCF-7 MDR | >100 | 78.8 | 80 |
| B16F10 | >100 | 73 | 16.9 |
| KB 3.1 | >100 | 50 | 2.96 |

TABLE 5-continued

IC50 of IFO, IFO-SQ and IFO-thio-SQ on each cell line tested.

| IC50 (μM) | Ifosfamide | Ifosfamide SQ | Ifosfamide-thio-SQ |
|---|---|---|---|
| M109 | >100 | >100 | 9.2 |
| MiaPaCa-2 | >100 | 32.5 | 4.4 |
| SK-N-MC (Ewing) | >100 | >100 | 19 |
| UW 479 (Glioma) | >100 | >100 | 65 |
| IGR-OV1 (Ovary) | >100 | >100 | 81 |

II. Evaluation of In Vivo Efficacy

In vivo cytotoxic efficacy was evaluated first on a model of human rhabdomyosarcoma xenografted in nude mice. The model used is the RD human pediatric rhabdomyosarcoma model. The cells were first amplified in culture and counted. $10.10^6$ cells were injected subcutaneously in both flanks of each mouse. After graft uptake, when tumor volume reached >80 mm$^3$, the mice were treated with IFO-SQ or placebo. Preliminary results of this study showed a significant decrease in tumor volume in mice treated with IFO-SQ compared to mice treated with placebo. Similar results are expected for the compound IFO-thio-SQ.

The invention claimed is:

1. A compound of formula (I)

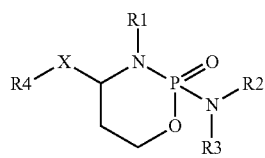

wherein
X is O or S;
R2 is H;
R1 and R3 are independently —(CH$_2$)$_2$—Cl or —CH(CH$_3$)—CH$_2$—Cl; and
R4 is a formulation or vectorization group comprising:
  a linear or branched unsaturated hydrocarbon group of 5 to 30 carbon atoms, optionally substituted by one or more groups selected from the group consisting of —OR, —C(O)OR, —OC(O)R, —OC(O)OR, —C(O)R, —NRR', —C(O)NRR', —NC(O)R, —NRC(O)R', —SR, halogen, cyano (—CN), aryl, heteroaryl, alkyl and arylalkyl;
  R is hydrogen or a C$_1$-C$_3$ alkyl and
  R' is hydrogen or a C$_1$-C$_3$ alkyl;
or a pharmaceutically acceptable salt thereof.

2. The compound according to claim 1, wherein R1 and R3 are both either —(CH$_2$)$_2$—Cl or —CH(CH$_3$)—CH$_2$—Cl.

3. The compound according to claim 1, wherein R4 comprises the linear unsaturated hydrocarbon group of 5 to 30 carbon atoms.

4. The compound according to claim 1, wherein R4 is a squalenoyl group.

5. The compound according to claim 4, wherein R2 is H, R1 and R3 are —(CH$_2$)$_2$—Cl, R4 is a squalenoyl group, and X is O or S.

6. The compound according to claim 1, wherein said compound is:

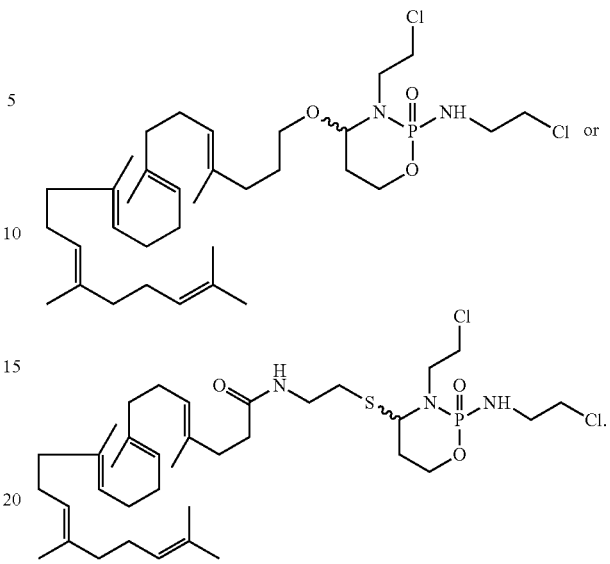

7. The compound according to claim 1, wherein R4 comprises one or several isoprene units.

8. The compound according to claim 1, wherein R4 is of formula R5(Y)$_a$ wherein:
Y is a spacer selected from the group consisting of —(CH$_2$)$_m$—, —CONH(CH$_2$)$_m$—, —NHCO(CH$_2$)$_m$—, —COO(CH$_2$)$_m$— and —OCO(CH$_2$)$_m$— wherein m is an integer ranging from 1 to 10;
a is 0 or 1; and
R5 is a linear and unsaturated hydrocarbon group of 5 to 30 carbon atoms optionally substituted by one or more methyl or hydroxyl groups.

9. The compound according to claim 1, wherein R4 is of formula R5(Y)$_a$ wherein:
Y is a spacer selected from the group consisting of —(CH$_2$)$_m$—, —CONH(CH$_2$)$_m$—, —NHCO(CH$_2$)$_m$—, —COO(CH$_2$)$_m$— and —OCO(CH$_2$)$_m$— wherein m is an integer ranging from 1 to 10;
a is 0 or 1; and
R5 is an unsaturated C$_5$-C$_{30}$ hydrocarbon group comprising one or more isoprene units.

10. The compound according to claim 9, wherein R5 is selected from the group consisting of:
(a) (CH$_3$)$_2$C=CH—CH$_2$—CH$_2$—[C(CH$_3$)=CH—CH$_2$—CH$_2$]$_m$— wherein m is an integer ranging from 0 to 5, and
(b) (CH$_3$)$_2$C=CH—CH$_2$—CH$_2$—[C(CH$_3$)=CH—CH$_2$—CH$_2$]$_p$—[CH=C(CH)$_3$—CH$_2$—CH$_2$]$_q$—
wherein p is an integer ranging from 1 to 5 and q is an integer ranging from 1 to 5.

11. The compound according to claim 1, wherein R4 comprises the branched unsaturated hydrocarbon group of 5 to 30 carbon atoms.

12. The compound according to claim 1, wherein R4 comprises the unsaturated hydrocarbon group of 5 to 30 carbon atoms branched with one or more methyl groups.

13. A nanoparticle formed by the compound according to claim 1; or a pharmaceutically acceptable salt thereof.

14. A nanoparticle comprising a compound according to claim 9.

15. A pharmaceutical composition comprising a compound according to claim 1.

16. A pharmaceutical composition comprising a nanoparticle according to claim 13.

17. A method for preparing a derivative of oxazaphosphorine of formula (I)

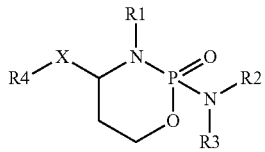
(I)

wherein
X is O or S;
R2 is H;
R1 and R3 are independently —(CH$_2$)$_2$—Cl or —CH(CH$_3$)—CH$_2$—Cl; and
R4 is a formulation or vectorization group comprising:
a linear or branched unsaturated hydrocarbon group of 5 to 30 carbon atoms, optionally substituted by one or more groups selected from the group consisting of —OR, —C(O)OR, —OC(O)R, —OC(O)OR, —C(O)R, —NRR', —C(O)NRR', —NC(O)R, —NRC(O)R', —SR, halogen, cyano (—CN), aryl, heteroaryl, alkyl and arylalkyl;
R is hydrogen or a C$_1$-C$_3$ alkyl and;
R' is hydrogen or a C$_1$-C$_3$ alkyl;
or a pharmaceutically acceptable salt thereof,

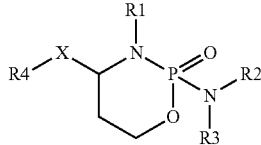

said method comprising:
providing a compound of formula (II)

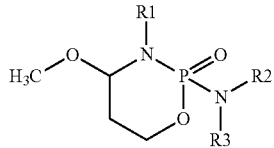
(II)

wherein R1, R2 and R3 are as defined in formula (I); and
reacting the compound of formula (II) with an alcohol or a thiol of formula (III) R4-XH, wherein X and R4 are defined as in formula (I), in the presence of a Lewis acid, said Lewis acid being BF$_3$OEt$_2$.

18. The method according to claim 17, wherein R2 is H, and R1 and R3 are both either —(CH$_2$)$_2$—Cl or —CH(CH$_3$)—CH$_2$—Cl.

19. The method according to claim 17, wherein R4 comprises one or several isoprene units.

20. The method according to claim 17, wherein R4 is of the formula R5(Y)$_a$ wherein:
Y is a spacer selected from the group consisting of —(CH$_2$)$_m$—, —CONH(CH$_2$)$_m$—, —NHCO(CH$_2$)$_m$—, —COO(CH$_2$)$_m$— and —OCO(CH$_2$)$_m$— wherein m is an integer ranging from 1 to 10;
a is 0 or 1; and
R5 is an unsaturated C$_5$-C$_{30}$ hydrocarbon group comprising one or more isoprene units.

21. The method according to claim 17, wherein R4 is a squalenoyl group.

22. A method for treating a patient suffering from a cancer, the method comprising administering said patient with a therapeutically effective dose of a pharmaceutical composition according to claim 15.

23. A method for treating a patient suffering from a cancer, the method comprising administering said patient with a therapeutically effective dose of a pharmaceutical composition according to claim 16.

* * * * *

UNITED STATES PATENT AND TRADEMARK OFFICE
CERTIFICATE OF CORRECTION

PATENT NO.        : 9,073,957 B2                                    Page 1 of 1
APPLICATION NO.   : 13/992404
DATED             : July 7, 2015
INVENTOR(S)       : Angelo Paci et al.

It is certified that error appears in the above-identified patent and that said Letters Patent is hereby corrected as shown below:

In the Specification

Column 7,
Lines 40-41, "formula —$H_2C=CH(CH_2)_m$—" should read --formula -$H_2C=CH(CH_2)_n$- --.

In the Claims

Column 28,
Line 28, "a is 0or 1;" should read --a is 0 or 1;--.

Signed and Sealed this
Twelfth Day of April, 2016

Michelle K. Lee
*Director of the United States Patent and Trademark Office*